United States Patent
Berrigan

Patent Number: 5,871,478
Date of Patent: Feb. 16, 1999

[54] IMPLANTABLE DRUG DELIVERY MEANS

[76] Inventor: Thomas John Berrigan, 38 Dumfries Road, Floreat Park, Western Australia, Australia

[21] Appl. No.: 591,450
[22] PCT Filed: Aug. 11, 1994
[86] PCT No.: PCT/AU94/00469
§ 371 Date: Jan. 31, 1996
§ 102(e) Date: Jan. 31, 1996
[87] PCT Pub. No.: WO95/04571
PCT Pub. Date: Feb. 16, 1995

[30] Foreign Application Priority Data
Aug. 11, 1993 [AU] Australia ................... PM0483

[51] Int. Cl.⁶ .................................................. A61M 9/22
[52] U.S. Cl. ................. 604/891.1; 604/132; 604/153; 128/DIG. 12
[58] Field of Search ...................... 604/9, 10, 93, 604/131, 132, 175, 185, 891.1, 151, 153; 128/DIG. 12

[56] References Cited

U.S. PATENT DOCUMENTS

| | | |
|---|---|---|
| 4,525,165 | 6/1985 | Fischell ................. 604/131 |
| 4,588,394 | 5/1986 | Schulte . |
| 4,681,560 | 7/1987 | Schulte . |
| 4,714,462 | 12/1987 | DiDomenico ................. 604/67 |
| 4,813,951 | 3/1989 | Cannon ................. 604/891.1 |
| 5,053,031 | 10/1991 | Borsanyi ................. 604/891.1 |
| 5,085,644 | 2/1992 | Watson . |

FOREIGN PATENT DOCUMENTS

| | | |
|---|---|---|
| 202696 | 11/1986 | European Pat. Off. . |
| 335671 | 10/1989 | European Pat. Off. . |
| 342946 | 11/1989 | European Pat. Off. . |
| 420620 | 4/1991 | European Pat. Off. . |
| 488701 | 6/1992 | European Pat. Off. . |
| 87/06473 | 11/1987 | WIPO . |

Primary Examiner—Danton D. DeMille
Attorney, Agent, or Firm—Ladas & Parry

[57] ABSTRACT

A subcutaneous drug delivery means which comprises a holding reservoir (11), a pumping means (15), a delivery reservoir (18) and an outlet (21). The holding reservoir (11) is connected to the delivery reservoir (18) through the pump (15) which is operable manually to deliver fluid from the holding reservoir (11) to the delivery reservoir (18). The delivery reservoir (18) is resiliently expandable from a minimum volume to a maximum volume and is connected to the outlet (21) through a flow restriction means (23) which controls flow to the outlet.

27 Claims, 3 Drawing Sheets

IMPLANTABLE DRUG DELIVERY MEANS

THIS INVENTION resides in a drug delivery means.

BACKGROUND OF THE INVENTION

In the treatment of patients it is often desirable to provide a means whereby a drug or like agent can be introduced in a controlled manner over an extensive period of time. With the conventional intake of drugs and the like by means of periodic ingestion of a capsule or tablet, or periodic injection, there is usually an initial increase in the amount of the active agent in the body which is then reduced over a period of time, until the next tablet is taken or injection given.

In many cases it is preferable to provide an intake of drug in a controlled manner such that the amount of drug in the body remains substantially constant. This is particularly the case in the treatment of patients suffering constant pain as in the case of terminally ill patients who require a constant amount of an analgesic to be administered in order for them to be able to withstand the pain.

In the past several devices have been proposed for controlling the introduction of the drug into a body whereby it can be delivered in a controlled manner over a period of time. Such devices have comprised pumps driven by a power source, and which controls the delivery of drug to the body. Some of these pumps may be mounted externally to the body and are connected to a catheter introduced to a the body of the patient. Other devices have comprised pump which is mounted subcutaneously to the body of the patient and which delivers a drug to the body at a desired location. Such devices suffer the disadvantage however they are quite expensive and that they utilize a power source in order to effect the delivery of the drug. In the event of the failure of the power source, the pump must be replaced. The power source has in the past taken a variety of forms including utilization of a phase-change fluid as is the case of a device marketed under the Trade Mark "INFUSAID".

Other delivery devices have comprised a manually operated pump which may be mounted externally to the body or subcutaneously in the body of the patient whereby the pump can be activated by the patient for the delivery of the drug as need arises for that drug. Examples of such devices are disclosed in U.S. Pat. Nos. 4,588,394, 4,681,560 and, 5,085,644 the contents of which are included herein by reference, and comprise devices whereby a pumping chamber is connected via catheter directly into the body and derives its source of drug from a holding reservoir. The pumping chambers are of the form whereby they are biassed to a maximum volume condition, and on activation by the patient it is moved to a minimum volume position. In the case of U.S. Pat. No. 5,085,644 the re-entry of the drug into the pumping chamber is controlled by means of a capillary such that the pump is only able to deliver a full volume after a predetermined period of time. The disadvantage with this form of delivery means however is that drug levels within the body will vary periodically whereby on activation of the pump, the drug level within the body initially has a high level which is then allowed to decay over a period of time until the pump is reactivated.

SUMMARY OF THE INVENTION

It is an object of this invention to provide a drug delivery means whereby the delivery of the drug to the patient can be controlled in order that there is a substantially constant delivery of the drug without the need for any form of a power source.

Accordingly the invention resides in a drug delivery means comprising a holding reservoir, a pump, a delivery reservoir and an outlet, said holding reservoir being connected to said delivery reservoir through said pump, said pump being operable manually whereby fluid is transferred from the holding reservoir to the delivery reservoir, said delivery reservoir being connected to the outlet through a flow restriction means which controls flow to the outlet, said delivery reservoir being formed to be resiliently expandable from a minimum volume to a maximum volume whereby the pressure induced on the fluid within the delivery reservoir between its minimum and its maximum volume is substantially constant and wherein the connection between the holding reservoir and the delivery reservoir permits flow only from the holding reservoir to the delivery reservoir while the pressure within the delivery reservoir is less than a predetermined pressure, said connection having a control means for preventing further delivery of fluid from the pumping means to the delivery reservoir on the pressure within the delivery reservoir attaining a predetermined pressure.

In one form the control means comprises a first valve between the holding reservoir and the pump, and a second valve between the pump and the delivery reservoir, said first and second valves permitting unidirectional flow to the pump and delivery reservoir respectively when said delivery reservoir is not filled to its maximum volume..and the pressure within the delivery reservoir is less than the predetermined pressure, the second valve permitting flow to the holding reservoir while the pressure within the delivery reservoir is at least equal to the predetermined pressure.

According to an alternative form the control means incorporates a unidirectional flow first valve between the holding reservoir and pump and a relief chamber between the pump and the delivery reservoir, said relief chamber being resiliently expandable with the expandable portion of the wall of the chamber having a higher modulus of elasticity than the delivery reservoir whereby the expandable portion will expand on the pressure between the pump and delivery reservoir being at least equal to the predetermined pressure.

In another form the control means may comprise a relief valve located between the delivery reservoir and the holding reservoir which will permit flow from the delivery reservoir to the holding reservoir when the fluid pressure in the delivery reservoir is at least equal to the predetermined pressure.

According to a preferred feature the flow restriction means comprises a single passageway and a filter located upstream from the passageway.

According to a preferred feature of the invention the flow restriction means is formed with a plurality of flow pathways. In one form the flow restriction means may comprise a plurality of capillary passageways. In one form the flow restriction means comprises a porous element. The porous element can be formed of glass, ceramic or a like inert material.

The invention would be more fully understood in the light of the following description of one specific embodiment. The description is made with reference to the accompanying drawings of which:

DETAILED DESCRIPTION

Each of the embodiments are intended as subcutaneous implantable drug delivery means which are formed of a suitable material to enable the implantation within a body cavity without the danger of formation of adhesions or like conditions.

Figure 1:
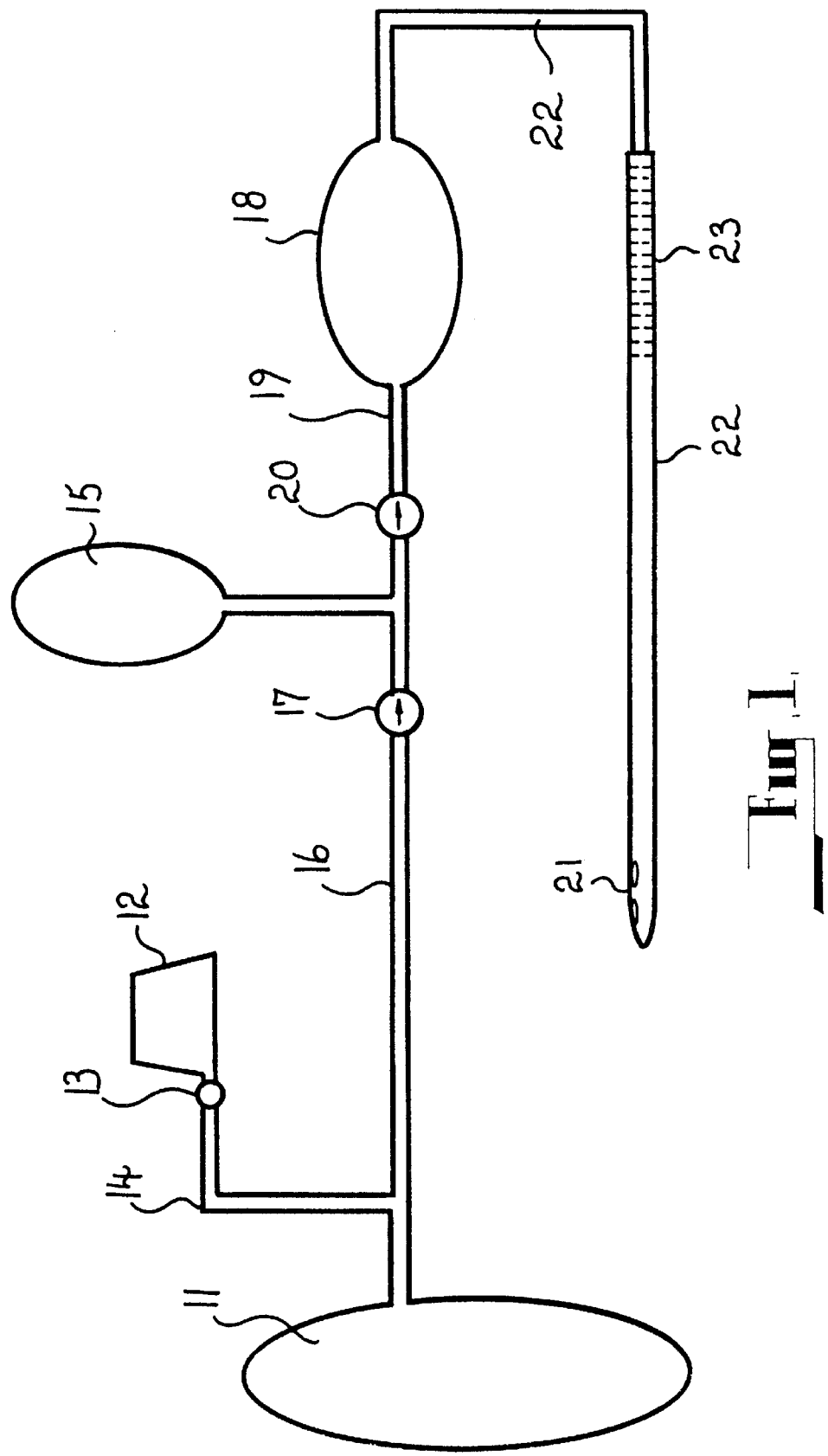
FIG. 1 is a schematic view of a first embodiment of the present invention.

The first embodiment as shown at FIG. 1 comprises a holding reservoir 11 which is associated with a injection port 12 which is also mounted within the body and which is adapted to receive the needle of an injection syringe whereby the holding reservoir 11 can be filled. The injection port 12 is connected through a filter 13 by means of an inlet duct 14. An example of a suitable part is disclosed in U.S. Pat. No. 5,137,529 the contents of which are incorporated herein by reference.

The delivery means further comprises a pump 15 which is connected to the holding reservoir 11 through a first delivery line 16. The flow of fluid through the first delivery line 16 to the pump 15, is controlled by means of a first valve 17. The pump comprises a patient activated pump which is located in a body cavity of the patient such that it is accessible to be manipulated by the patient. The pump comprises a chamber which is biassed to a maximum volume condition whereby on depression of the chamber as a result of manipulation by the patient, the chamber is caused to decrease in volume to deliver the contents of the chamber. The pump 15 is connected to a delivery reservoir 18 through a second delivery line 19. The flow of fluid from the pump 15 to the delivery reservoir 18 is controlled by means of a second valve 20. The delivery reservoir 18 is formed to be resiliently expandable or self inflating. To achieve this, at least a portion of the wall of the delivery reservoir 18 is resiliently expandable such that the delivery reservoir can be inflated.

The first valve 17 is essentially a unidirectional valve whereby there can be unidirectional flow, from the holding reservoir 11 to the chamber of the pump 15. The second valve 20 is primarily a unidirectional valve whereby there is a unidirectional flow of fluid from the chamber of the pump 15 to the delivery reservoir 18.

On the activation of the pump 15 by the patient causing the chamber of the pump 15 to collapse, fluid is delivered from the pump 15 into the delivery reservoir 18 and with repetitive activation of the pump 15 the delivery reservoir 18 is resiliently inflated to be filled by the drug.

The delivery reservoir is provided with a limiting means which serves to limit the volume of the delivery reservoir to a maximum whereby the delivery reservoir 18 is capable of expanding from a minimum volume condition to a maximum condition and whereby during such period of expansion a pressure is induced on the contents of the delivery reservoir by the resilient portion of the wall of the delivery chamber which is substantially constant throughout the expansion range of the delivery reservoir.

The means of controlling the maximum volume of the delivery reservoir may comprise a rigid container which surrounds the delivery reservoir 18 and which limits the expansion of the delivery reservoir beyond a maximum volume. Another alternative embodiment may comprise utilisation of reinforcing ribs or fibres accommodated within the expandable portion of the wall of the delivery reservoir which enables resilient expansion of that portion of the wall to a position corresponding to the maximum volume position of the delivery reservoir in order that there is substantially little expansion beyond that point. In another embodiment the means for controlling the maximum volume of the delivering reservoir may comprise a flexible enclosure having non expandable walls. The enclosure may be formed of a suitable cloth or mesh.

The first and second valves 17 and 20, while being unidirectional to allow for the delivery of fluid from the holding reservoir to the pump 15 and then to the delivery reservoir 18 are able to be rendered substantially bidirectional or unidirectional in the opposite direction at pressures above a predetermined pressure. Such valves are designed to allow flow in one direction at a specified primary pressure and then in the other direction at a secondary pressure. The effect of such is that on the delivery reservoir 18 attaining its maximum volume a back pressure is induced in the second delivery line 19, and then subsequently within the chamber of the pump 15 and the portion of the first delivery line 16 between the first valve 17 and the pump 15. On further activation of the pump, the relief property of the second valve 20 ensures that the pressure that can be induced within the delivery reservoir cannot exceed a predetermined level and this serves to prevent inflation of the delivery reservoir 18 beyond its maximum volume. This relief property of the first valve 17 also serves to ensure that on activation of the pump 15 when the delivery reservoir 18 is at it's maximum volume the contents of the chamber of the pump chamber 15 will be returned to the holding reservoir 11.

The delivery reservoir 18 is connected to an outlet 21 which may take any desired form according to the application of the delivery means through an outlet line 22. The outlet line 22 is provided with a flow restriction means 23 which comprises a means of ensuring a controlled flow from the delivery reservoir 18 to the outlet 21. The flow restriction means is formed with a plurality of passageways and may comprise an element having a plurality of capillary passageways or may comprise a porous element formed of glass, ceramic or a like inert material which is able to withstand the pressure created in the outlet line 22 by the delivery reservoir 18 such that a controlled quantity of fluid is allowed to pass through the flow restriction means.

The difference in volume of the delivery reservoir 18 between its minimum volume condition and its maximum volume condition is such that it is able to deliver the drug to the outlet 21 by means of the flow restriction means 23 over an extensive period of time.

In use the embodiment is mounted subcutaneously within the body of the patient with the injection port 12 being located at an appropriate injection site on the body and with the pump 15 located in a position at which it is accessible to the patient (e.g. above the sternum). The outlet 21 is located in the appropriate portion of the body according to the application of the embodiment. The dimensions of the device are such that the embodiment can be introduced into the body through a single small incision.

Once in position, the holding chamber 11 is filled with the drug through the injection port 12. To activate the embodiment, the pump 15 is then operated by the patient, by repetitive depression of the chamber of the pump 15 such that fluid is caused to flow from the holding reservoir, through the first delivery means 16, past the first valve 17, into the chamber of the pump 15, past the second valve 20 and through the second delivery lines 19 to the delivery reservoir 18. On the delivery reservoir 18 achieving its maximum volume any further activation of the pump 15 by the patient will not cause any further delivery into the delivery reservoir 18. Once the delivery reservoir 18 has sufficient fluid introduced into it causing it to expand beyond its minimum volume, a pressure will be exerted upon that fluid which will cause delivery to the outlet 21 through the flow restriction means 23. The rate of delivery is substantially constant. In use the patient would be instructed to activate the pump 15 at periods well short to the period of time required for the delivery reservoir 18 to contract from its maximum volume to its minimum volume such that the delivery reservoir 18 will maintain a volume corresponding substantially close to its maximum volume.

As a result of the embodiment, the drug is introduced into the patient from the outlet 21 at a substantially constant rate throughout its operating life. Furthermore because the flow restriction means 23 is provided with a plurality of passageways, the blockage of any one or more passageways does not prevent continued flow of fluid to the outlet 21 which insures that the embodiment can continue operating in the event of any such partial blockage.

Figure 2:
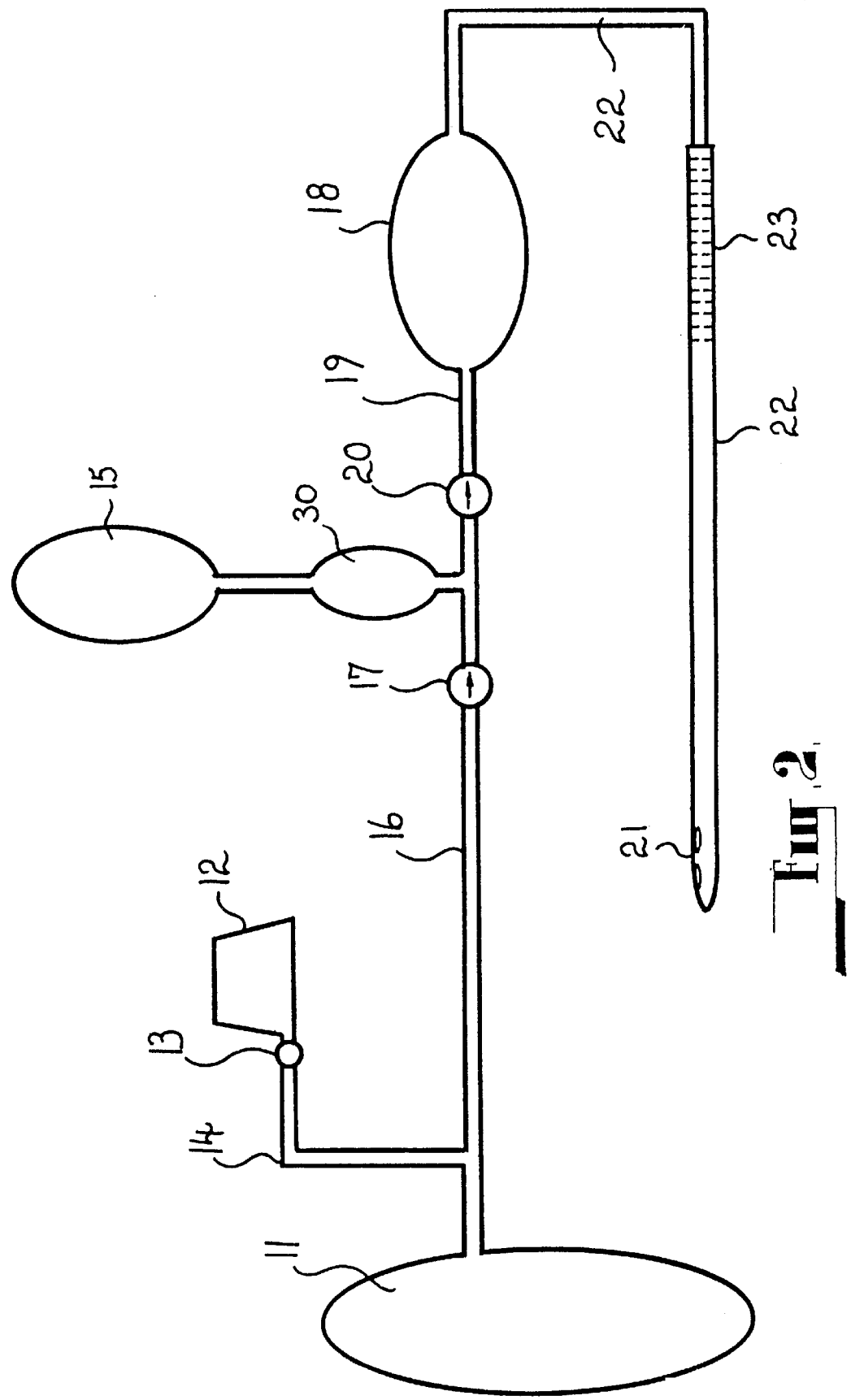
FIG. 2 is a schematic view of a second embodiment of the present invention.
Figure 3:
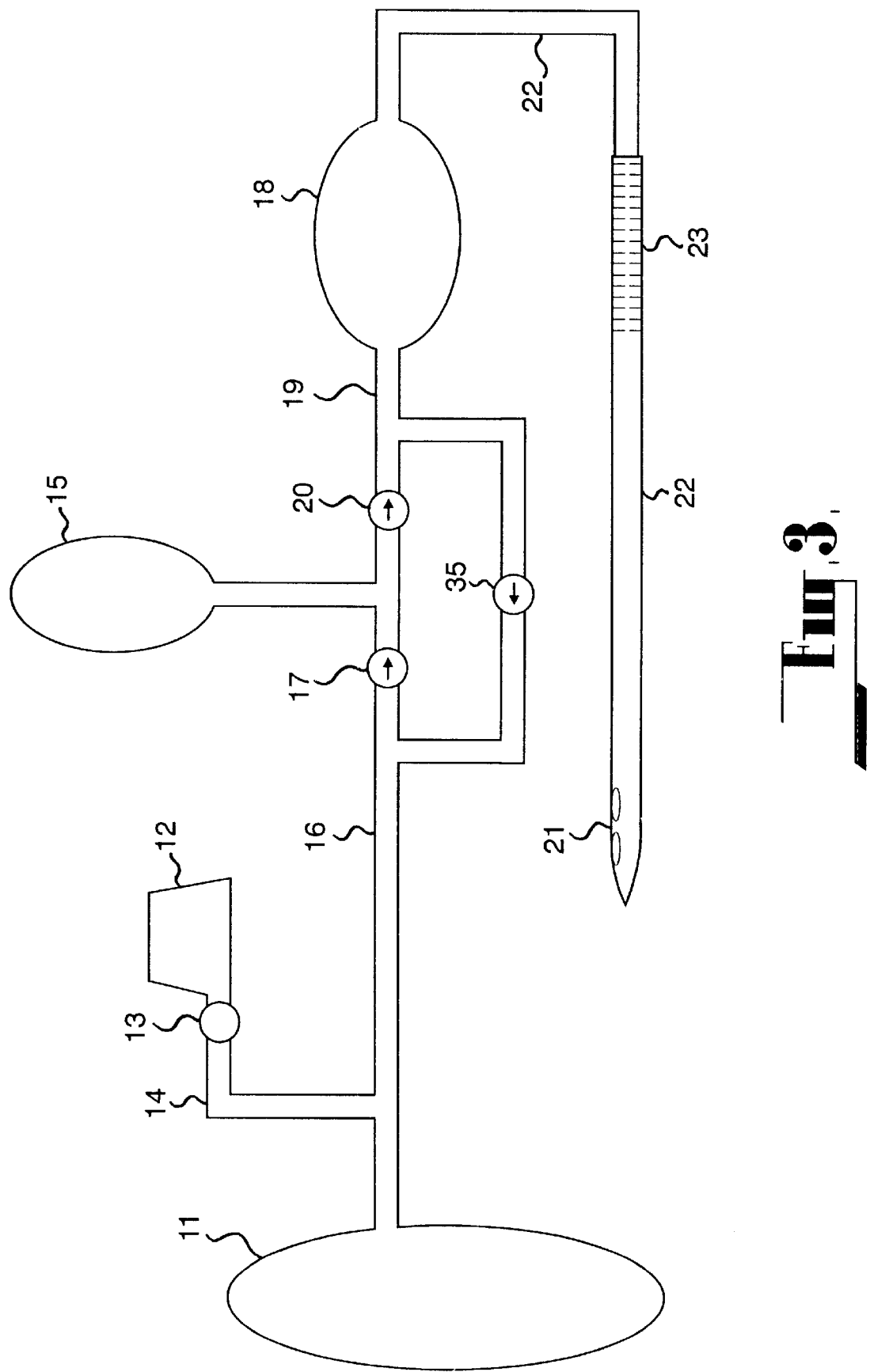
FIG. 3 is a schematic view of a third embodiment of the present invention.

The second embodiment as shown in FIG. 2 is of almost similar form to that of FIG. 1 and the description of the first embodiment is directly applicable to the second embodiment. As a result the same reference numerals have been used in FIG. 1 for corresponding components.

The difference between the first and second embodiments comprises the presence of a relief chamber 30 between the chamber of the pump 15 and the second valve 20. In addition, the first valve 17 and second valve 20 may comprise bidirectional valves of the form utilized in the first embodiment or alternatively may comprise unidirectional valves. The relief chamber 30 is formed to be resiliently expandable and the expandable walls of the chamber have a modulus of elasticity which is greater than that of the delivery reservoir 18. The effect of such is that on activation of the pump 15 causing the delivery of fluid to the chamber from the pump the delivery reservoir 18 is inflated in preference to the relief chamber 30 until such time as the delivery chamber 18 has achieved its maximum volume. On the delivery reservoir achieving its maximum volume, the back pressure created within the second delivery line 19 is such that as the pump 15 is activated causing collapse of its chamber, the relief chamber 30 is caused to inflate. On pressure being taken from the pump 15 to cause the natural expansion of the chamber of the pump, the fluid within the relief chamber is caused to return to the chamber of the pump 15 from the relief reservoir 30. Any continued activation of the pump 15 will merely cause inflation of the relief chamber 30 rather than any expansion of the delivery reservoir 18.

A third embodiment comprises a device of similar form to that of the first embodiment shown in FIG. 1 except the first and second valves 17 and 20 respectively are conventional unidirectional valves. In the case of the third embodiment, the delivery reservoir 18 is connected to the holding reservoir 11 through a third valve 35 comprising a relief valve which will open on the pressure in the delivery reservoir 18 exceeding a predetermined level. The pressure at which the relief valve 35 will open corresponds to the pressure which will be achieved after the delivery chamber has attained its maximum volume.

A fourth embodiment may take the form of any of the previous embodiments except that the flow restriction means comprises a single capillary having a filter upstream from the capillary to prevent blockage of the capillary.

It should be appreciated that the scope of the present invention may not be limited with the scope of the embodiment described above.

I claim:

1. A drug delivery device comprising a holding reservoir, a pump, a delivery reservoir and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable from a minimum volume to a maximum volume whereby the pressure induced on the fluid within the delivery reservoir between the minimum volume and the maximum volume provides a substantially constant rate of fluid delivery and wherein the connection between the holding reservoir and the delivery reservoir permits flow only from the holding reservoir to the delivery reservoir while the pressure within the delivery reservoir is less than a maximum pressure, said connection having a control means for redirecting flow to the holding reservoir upon the pressure within the delivery reservoir attaining said maximum pressure.

2. An implantable drug delivery device as claimed in claim 1 wherein the control means comprises a first valve between the holding reservoir and the pump and a second valve between the pump and the delivery reservoir, said first and second valve permitting unidirectional flow to the pump and the delivery reservoir respectively, while said delivery reservoir is not filled to its maximum volume and the pressure within the delivery reservoir is below the maximum pressure, the second valve permitting flow to the holding reservoir while the pressure within said delivery reservoir is at least equal to the maximum pressure.

3. A drug delivery device as claimed in claim 1 wherein the control means comprises a relief valve between the delivery reservoir and the holding reservoir which will permit flow from the delivery reservoir to the holding reservoir when the fluid pressure in the delivery reservoir is at least equal to the maximum pressure.

4. A drug delivery device as claimed in claim 1 wherein the flow restriction is provided with a plurality of flow pathways.

5. A drug delivery device as claimed in claim 4 wherein the flow restriction comprises a plurality of capillary passageways.

6. A drug delivery device as claimed in claim 4 wherein the flow restriction comprises a porous element.

7. A drug delivery device as claimed in claim 6 wherein the porous element is formed of glass, ceramic or like inert material.

8. A drug delivery device as claimed in claim 1 wherein the flow restriction comprises a single passageway and a filter located upstream from the passageway.

9. A drug delivery device as claimed in claim 1 wherein the delivery reservoir is enclosed by an enclosure having non-expandable walls to prevent the expansion of the delivery reservoir beyond the maximum volume.

10. A drug delivery device as claimed in claim 9 wherein the walls of the enclosure are rigid.

11. A drug delivery device as claimed in claim 9 wherein the walls of the enclosure are flexible.

12. A drug delivery device as claimed in claim 1 wherein the walls of the delivery reservoir are adapted to be incapable of expansion beyond the maximum volume.

13. A drug delivery device as claimed in claim 1 wherein the minimum volume comprises a volume of the delivery reservoir between the maximum volume and a reservoir minimum volume.

14. A drug delivery device comprising a holding reservoir, a pump, a delivery reservoir and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable from a minimum volume to a maximum volume whereby the pressure induced on the fluid within the delivery reservoir between the minimum volume and the maximum volume provides a substantially constant rate of fluid delivery and wherein the connection between the holding reservoir and the delivery reservoir permits flow only from the holding reservoir to the delivery reservoir while the pressure within the delivery reservoir is less than a maximum pressure, said connection having a relief chamber for receiving and accommodating fluid upon the pressure within the delivery reservoir attaining said maximum pressure.

15. An implantable drug delivery device as claimed in claim 14 wherein the control means comprises a first valve between the holding reservoir and the pump and a second valve between the pump and the delivery reservoir, said first and second valve permitting unidirectional flow to the pump and the delivery reservoir respectively, while said delivery reservoir is not filled to its maximum volume and the pressure within the delivery reservoir is below the maximum pressure, the second valve permitting flow to the holding reservoir while the pressure within said delivery reservoir is at least equal to the maximum pressure.

16. A drug delivery device as claimed in claim 14 wherein the control means comprises a one-way first valve between the holding reservoir and the pump, said relief chamber being located between the pump and the delivery reservoir, said relief chamber having a wall with an expandable portion and being resiliently expandable with the expandable portion of the wall of the relief chamber having a higher modulus of elasticity than the delivery reservoir whereby the expandable portion will expand on the pressure between the pump and delivery reservoir being at least equal to the maximum pressure.

17. A drug delivery device as claimed in claim 16 wherein a second one-way valve is mounted between the relief chamber and the delivery reservoir.

18. A drug delivery device as claimed in claim 14 wherein the flow restriction is provided with a plurality of flow pathways.

19. A drug delivery device as claimed in claim 18 wherein the flow restriction comprises a plurality of capillary passageways.

20. A drug delivery device as claimed in claim 18 wherein the flow restriction comprises a porous element.

21. A drug delivery device as claimed in claim 20 wherein the porous element is formed of glass, ceramic or like inert material.

22. A drug delivery device as claimed in claim 14 wherein the flow restriction comprises a single passageway and a filter located upstream from the passageway.

23. A drug delivery device as claimed in claim 14 wherein the delivery reservoir is enclosed by an enclosure having non-expandable walls to prevent the expansion of the delivery reservoir beyond the maximum volume.

24. A drug delivery device as claimed in claim 23 wherein the walls of the enclosure are rigid.

25. A drug delivery device as claimed in claim 23 wherein the walls of the enclosure are flexible.

26. A drug delivery device as claimed in claim 14 wherein the walls of the delivery reservoir are adapted to be incapable of expansion beyond the maximum volume.

27. A drug delivery device as claimed in claim 14 wherein the minimum volume comprises a volume of the delivery reservoir between the maximum volume and a reservoir minimum volume.

* * * * *